US008315766B2

(12) United States Patent
Rebut et al.

(10) Patent No.: US 8,315,766 B2
(45) Date of Patent: Nov. 20, 2012

(54) PROCESS FOR DETECTING A PHENOMENON LIMITING THE VISIBILITY FOR A MOTOR VEHICLE (75) Inventors: Julien Rebut, Paris (FR); Joël Leleve, Epinay sur Seine (FR); David Hue, Chatou (FR)

(73) Assignee: Valeo Vision, Bobigny (FR)

( * ) Notice: Subject to any disclaimer, the term of this patent is extended or adjusted under 35 U.S.C. 154(b) by 1002 days.

(21) Appl. No.: 12/260,235

(22) Filed: Oct. 29, 2008

(65) Prior Publication Data
US 2009/0118909 A1 May 7, 2009

(30) Foreign Application Priority Data
Oct. 31, 2007 (FR) ..................................... 07 07683

(51) Int. Cl.
G06F 7/00 (2006.01)
G06F 17/00 (2006.01)
(52) U.S. Cl. ............ 701/49; 701/36; 382/103; 382/173; 382/190; 348/149
(58) Field of Classification Search .......... 340/601–602; 701/36, 49; 706/919, 922; 382/100, 190, 382/206, 103, 173, 937–934, 174; 359/618; 348/149, 135, 435
See application file for complete search history.

(56) References Cited

U.S. PATENT DOCUMENTS

| 6,362,773 | B1 | 3/2002 | Pochmuller | |
|---|---|---|---|---|
| 7,944,362 | B2* | 5/2011 | Hue et al. | 340/602 |
| 7,949,190 | B2* | 5/2011 | Wu et al. | 382/206 |
| 8,090,194 | B2* | 1/2012 | Golrdon et al. | 382/154 |
| 8,208,719 | B2* | 6/2012 | Gordon et al. | 382/154 |
| 2003/0030638 | A1* | 2/2003 | Astrom et al. | 345/420 |
| 2003/0178487 | A1* | 9/2003 | Rogers | 235/454 |
| 2005/0200838 | A1* | 9/2005 | Shaw et al. | 356/237.1 |
| 2008/0118143 | A1* | 5/2008 | Gordon et al. | 382/154 |
| 2009/0118909 | A1* | 5/2009 | Rebut et al. | 701/49 |
| 2010/0020170 | A1* | 1/2010 | Higgins-Luthman et al. | 348/135 |
| 2010/0225762 | A1* | 9/2010 | Augst | 348/148 |
| 2011/0141242 | A1* | 6/2011 | Fernandez Alvarez et al. | 348/47 |

(Continued)

FOREIGN PATENT DOCUMENTS
DE 10303046 A1 10/2004
(Continued)

OTHER PUBLICATIONS

Horn, "Shape From Shading: A Method for Obtaining the Shape of a Smooth Opaque Object From One View," Technical Report 79, Project MAC, Massachusetts Institute of Technology (MIT), Cambridge, Massachusetts, USA, Nov. 1970, http://hdl.handle.net/1721.1/6885.*

(Continued)

Primary Examiner — Cuong H Nguyen
(74) Attorney, Agent, or Firm — Jacox, Meckstroth & Jenkins (57) ABSTRACT A process and system for detecting a phenomenon limiting the visibility for a motor vehicle. The process and system comprises the steps of determining at least one point of interest in an image captured of the environment of the vehicle (CALC_H(I)); determining a region of interest in the image (CALC_ROI(I)); determining a graph of different levels of grey on the basis of said region of interest (CALC_CL(ROI)), and determining an area in said graph of different levels of grey around said point of interest (CALC_A(CL, H)).

15 Claims, 6 Drawing Sheets

U.S. PATENT DOCUMENTS

2012/0063672 A1* 3/2012 Gordon et al. .............. 382/154

FOREIGN PATENT DOCUMENTS

| EP | 0687594 | A1 | 12/1995 |
| --- | --- | --- | --- |
| EP | 1067399 | A2 | 1/2001 |
| FR | 2847367 | A1 | 5/2004 |
| WO | 9716926 | A1 | 5/1997 |
| WO | 03069275 | A1 | 8/2003 |

OTHER PUBLICATIONS

Nitzan et al., "The Measurement and Use of Registered Reflectance and Range Data in Scene Analysis," Proceedings of the IEEE, vol. 65, No. 2, pp. 206-220, Feb. 1977.*

Night time vehicle detection for driving assistance lightbeam controller; Alcantarilla, P.F.; Bergasa, L.M.; Jimenez, P.; Sotelo, M.A.; Parra, I.; Fernandez, D.; Mayoral, S.S.; Intelligent Vehicles Symposium, 2008 IEEE; Digital Object Identifier: 10.1109/IVS.2008. 4621142; Publication Year: 2008 , pp. 291-296.*

Baj et al., "Automatic Measurement of Plate Coordinates in order to Obtain Automatic Plotting," ISPRS Archives, vol. XXV, Part A2, Commission II, pp. 28-37, XVth Congress, Rio de Janeiro, Brazil, Jun. 17-29, 1984.*

Hautiere, Nicolas et al., "Towards Fog-Free In-Vehicle Vision Systems Through Contrast Restoration"; Proceedings of the IEEE Computer Society Conference on Computer Vision and Pattern Recognition, Jun. 27, 2007.

* cited by examiner

PROCESS FOR DETECTING A PHENOMENON LIMITING THE VISIBILITY FOR A MOTOR VEHICLE

CROSS-REFERENCE TO RELATED APPLICATIONS

This application claims priority to French Application No. 0707683 filed Oct. 31, 2007, which application is incorporated herein by reference and made a part hereof.

BACKGROUND OF THE INVENTION

1. Field of the Invention

The present invention relates to a process for detecting a phenomenon that limits the visibility for a motor vehicle and a detection device enabling the implementation of said process.

The present invention applies in particular to the field of motor vehicles.

2. Description of the Related Art

When applied to a motor vehicle, a process for the detection of a phenomenon limiting the visibility, such as fog, known from prior art, uses a video image to detect high density fog at night. To this end, it uses the luminous halo that forms an ellipse, which is generated by the reflection of headlamps from the fog. Detection of the fog is effected as a function of the parameters of this ellipse.

One problem of this state of the art is that it does not enable fog of a light or medium density to be detected, because fog of this type does not generate a sufficiently visible halo to create an ellipse when it is illuminated by the vehicle's headlamps, with the result that such a halo cannot be used for the detection of fog.

SUMMARY OF THE INVENTION

The aim of the present invention is the detection of a phenomenon that limits the visibility, such as fog, especially during the night, regardless of the density of the fog.

According to a first object of the invention, this aim is achieved by a process for detecting a phenomenon limiting the visibility in the surroundings of a motor vehicle and comprises the following steps:
- the emission of a light beam into the vicinity of the motor vehicle by at least one of the vehicle's headlamps;
- the determination of at least one point of interest in an image captured within the environment of the vehicle;
- the determination of an area of interest within the image;
- the determination of a graph for different levels of grey based on the area of interest; and
- the determination of an area within the graph for different levels of grey in relation to the point of interest in question.

As will be seen in detail below, the area defined within the graph for different levels of grey will change in relation to the variations in the atmosphere surrounding a motor vehicle and also in front of the vehicle and thus in relation to the presence of fog, which will modify this atmosphere. This area will thus enable any fog, regardless of its density, to be detected and furthermore it will enable the density of the fog to be determined on the basis of the different values observed in the area. It is therefore not necessary for different methods, which are dependent on the density of the fog, to be used. Moreover, such a process is easily implemented.

According to non-limiting embodiments of the invention, the process also has the following characteristics:
- the process comprises a supplementary step for determining the presence of a phenomenon limiting the visibility in relation to at least one threshold value of the area. This enables the presence of a visibility limiting phenomenon not only to be detected but also for its density to be determined.
- the process comprises an additional step, which calculates a visibility distance in relation to the specific area. Finally, this enables a maximum driving speed to be given in order to guarantee an optimum safety distance.
- the point of interest is situated on the horizon line in the image. The horizon line is easily determined with image processing.
- the vehicle has a steering angle and the region of interest is determined in the image in relation to the steering angle. It is then possible to consider the direction of the road along which the vehicle is traveling and this provides a homogenous region of interest even if the road is winding.

According to a second object of the invention, the invention relates to a device for detecting a phenomenon limiting the visibility in the surroundings of a motor vehicle having:
- at least one headlamp to:
  - emit a light beam in the surroundings of the vehicle;
- a control unit to:
  - determine at least one point of interest in an image captured showing the surroundings of the vehicle;
  - determine a region of interest in the image;
  - determine a graph of levels of grey on the basis of the region of interest, and
  - determine an area within the graph of levels of grey in relation to the identified point of interest.

According to a third object of the present invention, the invention relates to a computer program containing one or more sequences of instructions that can be carried out by an information processing unit, with the execution of the sequences of instructions enabling the implementation of the process in accordance with any one of the above characteristics.

These and other objects and advantages of the invention will be apparent from the following description, the accompanying drawings and the appended claims.

BRIEF DESCRIPTION OF THE ACCOMPANYING DRAWINGS

Other characteristics and advantages of the present invention will be better understood by reading the following description and studying the following non-limiting drawings, among which.

DETAILED DESCRIPTION OF THE PREFERRED EMBODIMENTS

Figure 1:
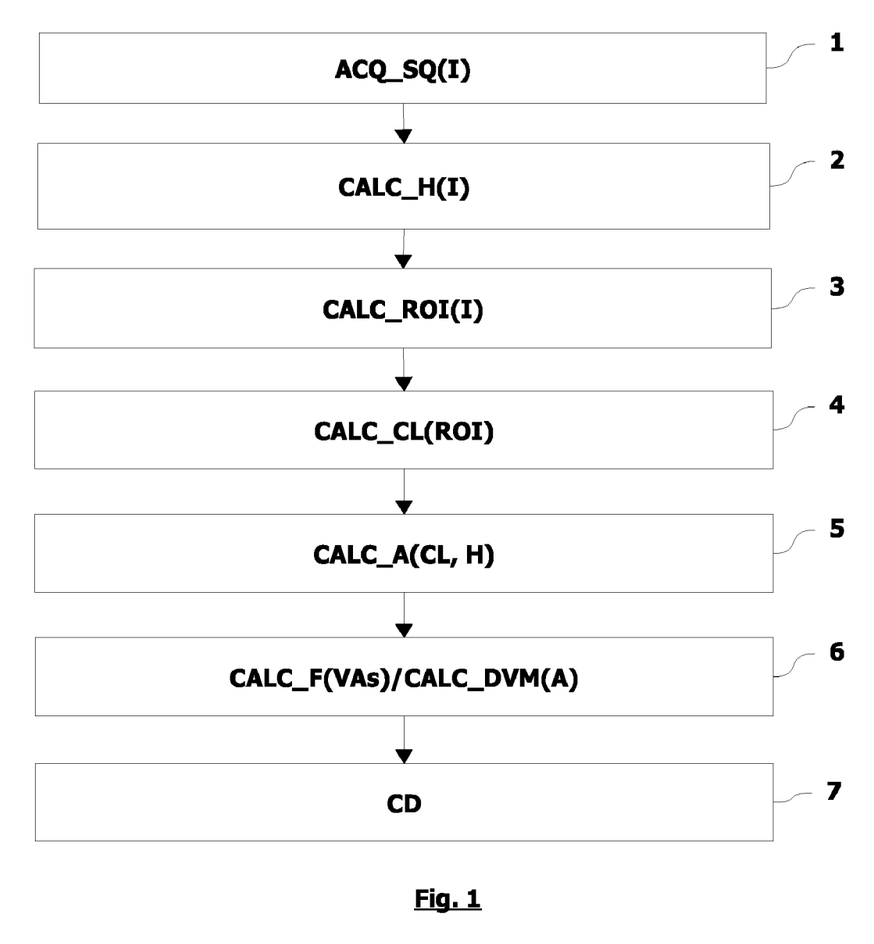
FIG. 1 represents a diagram of a non-limiting embodiment of the detection process according to the invention.

The process for detecting a phenomenon limiting the visibility in accordance with the present invention is illustrated in a non-limiting manner in FIG. 1.

In this application, the detection is effected by means of a detector device installed in a vehicle V, the vehicle comprising in particular:
headlamps, and
a video camera, described in further detail below.

In the present specification, a visibility limiting phenomenon F such as fog is taken as a non-limiting example.

Clearly, the process could be applied to other phenomena limiting the visibility, that is to say, any phenomenon F that causes an atmospheric disturbance of such a nature that it is likely to produce a loss of visibility for a user of a motor vehicle V, such as heavy rain or projections of water (known as Gischt in German and Spray in English) generated by vehicles driving in front of the vehicle V.

The detection process comprises the following steps as illustrated in FIG. 1:
determination at block 2 of at least one point of interest H in a captured image I of the situation around the vehicle V (step CALC_H(I));
determination at block 3 of a region of interest ROI in the image I (step CALC_ROI(I));
determination at block 4 of a graph of different levels of grey CL on the basis of the region of interest ROI (step CALC_CL(ROI));
determination at block 5 of an area A in the graph of different levels of grey CL in relation to the calculated point of interest H (step CALC_A(CL, H)).

In a non-limiting embodiment, the process according to the present invention also comprises an additional step for the purpose of:
determination at block 6 of the presence of fog F in relation to at least one threshold value VAs in the area A (step CALC_F(VAs)).

In a non-limiting embodiment, the process also comprises a supplementary step for:
determination at block 6 of a visibility distance DVM in relation to the defined area A (step CALC_DVM(A)).

It will be noted that these two embodiments can be combined.

In a non-limiting embodiment, the process also comprises a step for the:
capture of at least one image I by a camera (step ACQ_SQ (I)) at block 1.

It will be noted that this step for the capture of an image I can form no part of the process described, although this step can form part of another process carried out upstream of the process described.

The different steps are described in greater detail below.

In a first step 1), at least one image I is as captured by the camera mounted in the vehicle V.

If the video camera CAM is placed, as shown in the example given, in front of the vehicle V, the captured image I corresponds to the situation E outside a vehicle located within the field of the camera CAM and therefore in front of the vehicle V. In this way it is possible to detect a phenomenon F limiting the visibility such as fog in front of the vehicle V.

The light from the light beam of light FX emitted by one of the vehicle headlamps PJ is diffused in the presence of particles of the fog F in suspension in the atmosphere. As the wavelength of this light beam is compatible with the spectral analysis of the camera CAM, and as the particles that make up the fog F are located within the field of vision of the camera CAM, it is possible to capture an image comprising the diffused light in the fog F.

Figure 2:
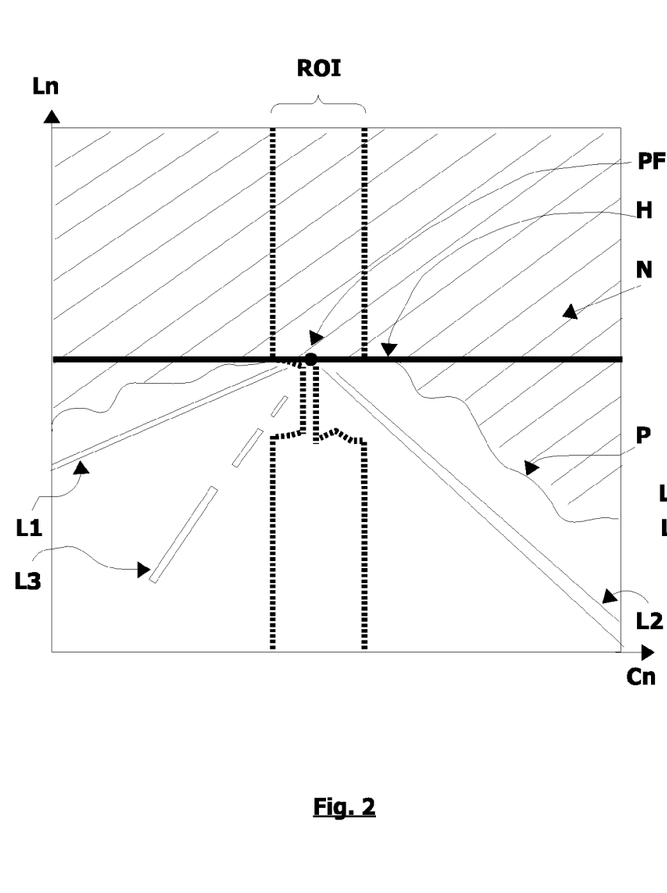
FIG. 2 is a schematic representation of an image of the surroundings of a vehicle acquired by the process shown in FIG. 1 in the absence of fog.
Figure 3:
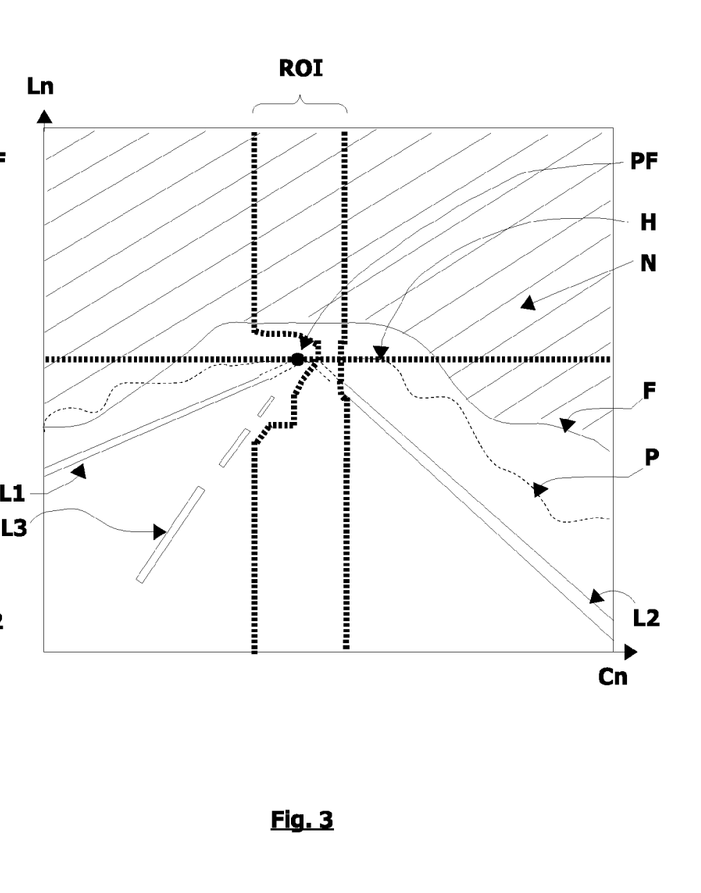
FIG. 3 is a schematic representation of an image of the surroundings of a vehicle acquired by the process shown in FIG. 1 in the presence of fog.

FIG. 2 illustrates a schematic example of such a captured image I taken at night without the presence of fog F, while FIG. 3 illustrates a schematic example of a captured image I taken at night with the presence of fog F. The columns Cn of this image I can be seen in the abscissa of an image I, while the lines Ln of this image I can be seen in the ordinate I.

These images I illustrate the appearance of the light diffused at night from a light beam FX emitted by the vehicle headlamps PJ.

The white part represents the light diffused at night from the light beam FX, while the diagonally shaded part, marked N, represents the environment outside E, here in front of the vehicle V, within the field of the camera CAM not illuminated by the light beam FX.

On the two figures FIG. 2 and FIG. 3, can be seen:
a road along which is traveling the vehicle V, represented by the two lateral road markings: lines L1 and L2, the central road marking: line L3; and
landscape P bordering the road.

In FIG. 3, the landscape P bordering the road is shown by a dotted line, because it is veiled by the fog F, which is schematically represented.

In a second step 2), at least one point of interest H is determined in an image I captured of the environment E outside the vehicle V.

In a non-limiting embodiment, this point of interest is situated along the line of the horizon H in the captured image I.

In the non-limiting examples, it is possible to determine the horizon line H from a calculated vanishing point PF in the image I obtained by the intersection of the white lines L1 and L2 on the road, or alternatively from car attitude sensors.

The determination of the horizon line H in an image being well known to the man skilled in the art, it will not be described in detail in the present description.

It will be noted that determining the horizon line H as a point or points of interest is easy to calculate.

The horizon line H is shown in both FIGS. 2 and 3.

In FIG. 3, the horizon line H is shown in the form of a dotted line, because it is veiled by the fog F.

In a third step 3), a region of interest ROI is determined in the image I.

In non-limiting examples, the region of interest ROI can be:
a vertical straight line passing through a reference point PR in the image I,
determined in the vicinity of a reference point PR by a surface situated on both sides of the reference point as illustrated by dotted lines in FIG. 2 and FIG. 3.

In a non-limiting embodiment, the reference point PR is the vanishing point PF as illustrated in FIG. 2 and FIG. 3.

In a variant to this embodiment, the vanishing point PF is centered on the captured image I. In this way, for a typical image I with a format of 640*480, its abscissa PFx is situated at 320 pixels and its ordinate PFy is on the horizon line H. It is assumed that in this situation, the optical axis of the camera CAM is parallel to the direction of travel of the vehicle V.

A region of interest ROI according to the second embodiment can be determined in the following manner, in a non-limiting embodiment:

in a first step, the contours in the image I are determined in such a manner as to remove the non-homogenous zones of the image I, with the aim of having the same average level of grey. In non-limiting examples, contour detection methods (known in English as 'edge methods') such as the Sobel, Prewitt, Roberts, Zero-cross, Canny methods etc. can be used;

in a second step, the region of interest ROI is determined from the horizon line H and by using a region increasing algorithm towards the top and towards the bottom of the captured image I, a technique that is well known to the man skilled in the art. It will be noted that, in order to determine the horizon line H, it is possible in non-limiting examples, to determine this horizon line on the basis of a calculation of a vanishing point PF in the image I, calculated by the intersection of the white lines L1 and L2 of the road markings, or alternatively by the use of car attitude sensors. The determination of the horizon line H in an image being already known to the man skilled in the art, it will not be described in further details in the present specification.

In this way, a homogeneous region of interest ROI can be obtained, in which are excluded:

noise, parasites; and non-homogeneous objects such as vehicles, or white lines along the road, such as the line L3, as illustrated in FIG. 2 and FIG. 3.

In a non-limiting embodiment, in order to arrive at a homogenous region of interest ROI, even in the case of a winding road, the region of interest ROI is further determined in the image I as a function of the angle α of the steering wheel of the vehicle V.

In a first non-limiting alternative embodiment:

the region of interest ROI is centered relative to the reference point PR (see above) in the image I, while the angle α of the steering wheel is null; and the region of interest ROI is offset laterally relative to the reference point PR in image I when the steering wheel angle α is not null. In a non-limiting example, the region of interest ROI is offset three times the steering wheel angle α.

In this way, when the steering wheel angle α is positive, the region of interest ROI is offset to the right on the image I, whereas when the steering wheel angle α is negative, the region of interest is offset to the left in the image I. For example, if the steering wheel angle α is 10°, the region of interest ROI is offset by 30 pixels to the right relative to the reference point PR, and is thus centered on a new reference point of 320+30 pixels.

In a second non-limiting alternative embodiment:

the region of interest ROI is centered relative to the reference point PR (as seen above) in the image I, when the steering wheel angle α is less than or equal to 15° in absolute value; and the region of interest ROI is offset laterally relative to the reference point PR in the image I, when the steering wheel angle α is greater than 15° in absolute value. In a non-limiting example, the region of interest ROI is offset three times the steering wheel angle α. This threshold value of 15° is characteristic of a winding road. When the steering wheel angle α is less than 15° in absolute value, the road is, in general, straight, but it is the driver of the vehicle V who does not drive straight.

Therefore, if the steering wheel angle α is greater than +15°, the region of interest ROI is offset to the right on the image I (the road turns to the right), while if the steering wheel angle α is less than −15°, the region of interest ROI is offset on the left of the image I (the road turns to the left).

For example, if the steering wheel angle α is −18°, the region of interest ROI is offset by 54 pixels to the left relative to the reference point PR and is therefore centered on a new reference point of 320-54 pixels.

In this way, determining the position of the region of interest ROI (and more particularly its position relative to the axis of the abscissas as described above) in the image I captured relative to the steering wheel angle α, means that the direction of the road can be taken into account and oncoming obstacles such as slopes, trees etc. can be avoided in cases where the road is winding. The region of interest ROI is thus more homogenous.

It will be noted that the second and the third steps can be carried out in parallel if necessary.

In a fourth step 4), a graph of the different levels of grey CL is determined on the basis of the region of interest ROI.

The interest is that the presence of fog F will affect the shape of the graph of the different levels of grey CL in such a way that, by studying the graph, the presence of fog F can be determined.

In a non-limiting embodiment, this graph of the different levels of grey CL is determined in the following manner. For each line Ln of the captured image I, only the pixels of the region of interest ROI are considered and a combination of pixels Px is applied for obtaining a value GR for each line, with this value GR being for example a value for a level of grey in the case of a video image (as described below).

In a typical non-limiting embodiment, the combination is the median value of the levels of grey of each pixel Px of the line Ln in question. The advantage of the median line is that it estimates the average value of the levels of grey, while at the same time, resolving the problems of noises in the image I.

Figure 4:
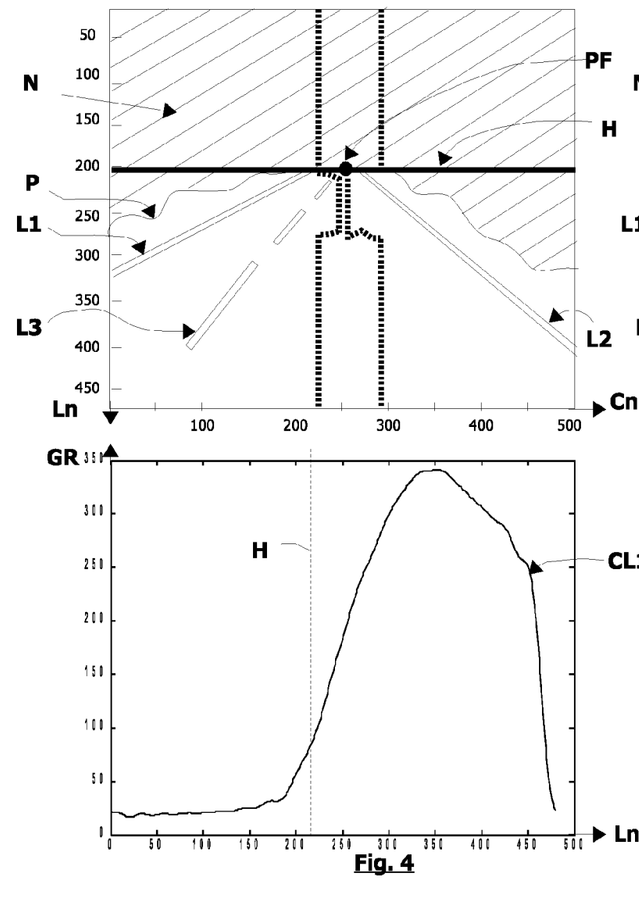
FIG. 4 represents the image shown in FIG. 2 and an associated graph of levels of grey.
Figure 5:
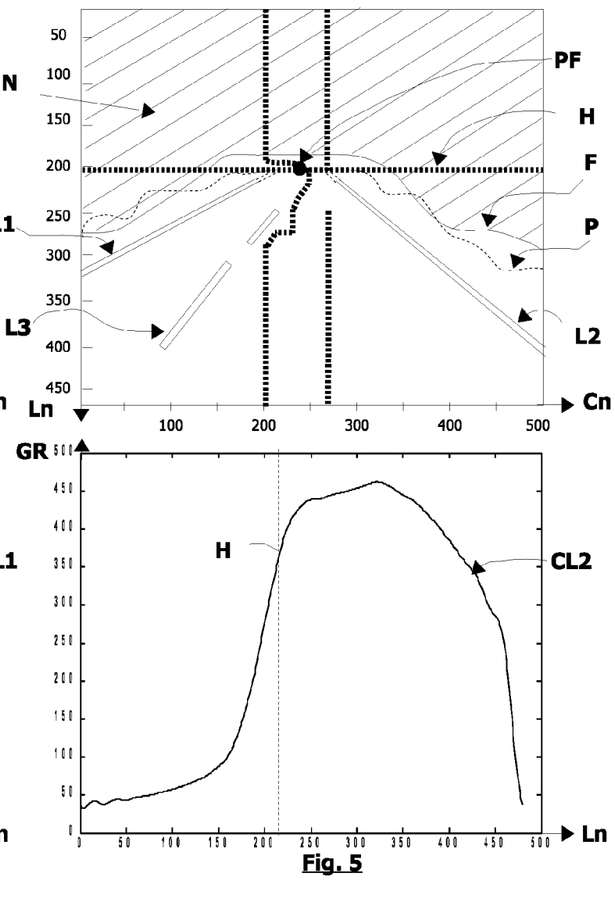
FIG. 5 represents the image shown in FIG. 3 and an associated graph of levels of grey.

FIG. 4 contains a first example of a graph of levels of grey CL1 in a situation when there is no fog F, while FIG. 5 contains a second example of a graph of levels of grey CL2 when fog F is present.

As can be seen, for a graph of different levels of grey CL, the line number Ln is shown in abscissa in the captured image I, while the value attributed to the level of grey GR is shown in the ordinate.

A horizon line H has been added to both of these graphs of different levels of grey CL1 and CL2 and it is situated at around the abscissa 220.

It will be noted that where the integration time of the camera CAM is known, such a graph CL can be, in non-limiting embodiments, either a luminance curve or a luminosity curve.

It will be reminded that the integration time of the camera CAM represents the time during which the camera sensors are exposed to the light.

In a fifth step 5), an area A is determined in the graph of different levels of grey CL relative to the specific point of interest H.

As will be seen, by studying the area A in this graph, it will be possible to determine the presence of fog F.

In a non-limiting embodiment, this area A is determined relative to the horizon line H, with the point of interest being situated on the horizon line H as seen above.

In a first non-limiting alternative embodiment, this area A is the area that corresponds to the top of the captured image I up to the horizon line H. It is therefore the area that is situated above the horizon line H.

The advantage of this alternative is that it is possible to obtain a graph of the different levels of grey reference CL1 without the presence of fog, which is independent of parameters such as the infrastructure of the road (e.g. the type of covering, the amount of moisture on the road etc.). The area A1 in the reference curve obtained in this manner will therefore be close to being constant without fog and the graph CL1 thus obtained will be stable (the top of the image is black).

As will be seen below, when fog F is present, the area A2 in the graph of the different levels of grey CL2 is different from the area A1 of the graph reference CL1 and it will be simple to analyze this graph relative to the reference graph CL1, which is stable, in order to establish the presence of fog.

Furthermore, the advantage of this alternative is that there is no diffusion of light above the horizon line H, due to the light from the vehicle's headlamps, when there is no fog F present although this light diffusion exists when fog F is present, the diffusion being caused by the reflection of the light beam FX from the vehicle's headlamps on the particles of fog F. A study of the graph of different levels of grey enables this diffusion of light to be identified.

It will be noted that, in a second alternative non-limiting embodiment, this area A is the area that corresponds to bottom of the captured image I as far as the horizon line H.

Figure 6:
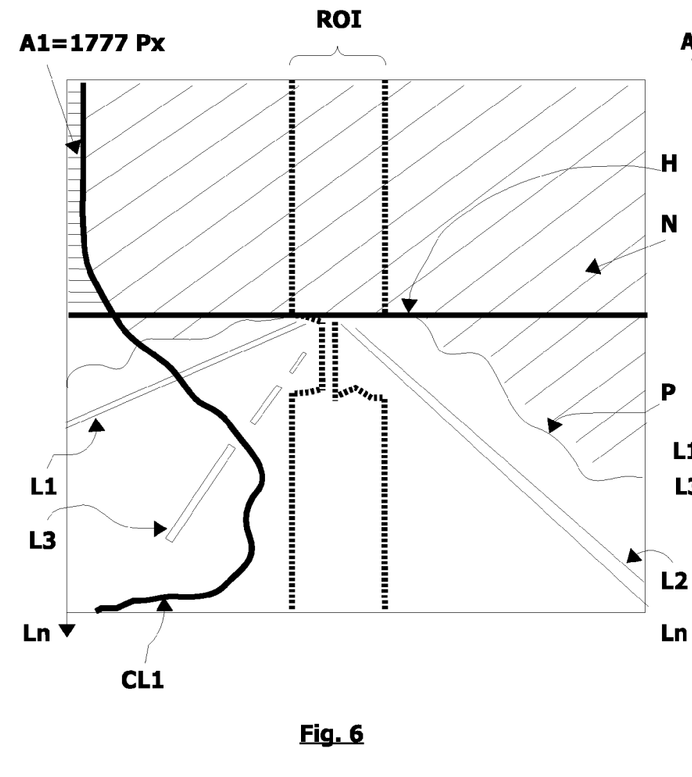
FIG. 6 represents the image shown in FIG. 2, on which an associated graph of levels of grey has been superimposed and an area within this graph of levels of grey.
Figure 7:
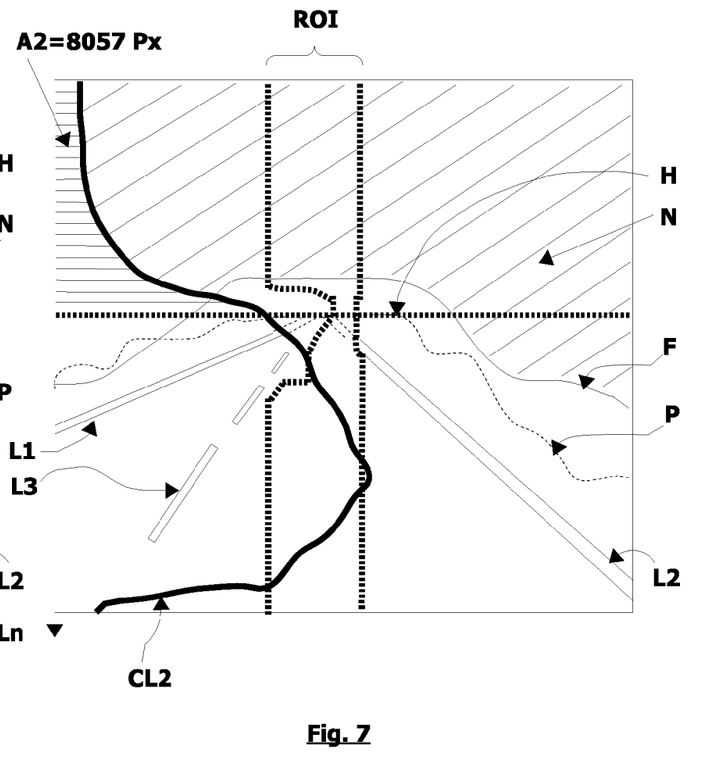
FIG. 7 represents the image shown in FIG. 3, on which an associated graph of levels of grey has been superimposed and an area within this graph of levels of grey.

As can be seen in FIGS. 6 and 7, the graphs of the different levels of grey CL1 and CL2 associated respectively with the images I captured in the absence of fog F and in the presence of fog F are superimposed on the associated images I (they have been rotated through 90° relative to the examples of the graphs shown in FIGS. 4 and 5 above).

A first area A1 and a second area A2 associated respectively with the first graph of the different levels of grey CL1 and the second such graph CL2 are shown (horizontal shading) respectively in FIGS. 6 and 7 in accordance with the first alternative embodiment (top of the image).

In a sixth step 6), both the presence of fog F and its density are determined.

In a first embodiment, the presence of fog F and its density are determined in relation to at least one threshold value VAs of the area A.

More particularly, the presence of fog F and its density are determined in relation to a number of threshold values VAs, which will enable to define that:

the vehicle is approaching/leaving an area containing fog F;

the vehicle is in an area containing fog F and also to define that:
the density of the fog F is low;
the density of the fog F is moderate; and
the density of the fog F is high.

It will be noted that the density of the fog F is in relation to a visibility distance DVM.

In this way, when the fog F is of:
low density, the corresponding visibility distance DVM is above 100 meters (between 100 and 150 meters for example);
moderate density, the corresponding visibility distance DVM is between 60 meters and 100 meters; and
high density, the corresponding visibility distance DVM is less than 60 meters.

Figure 8:
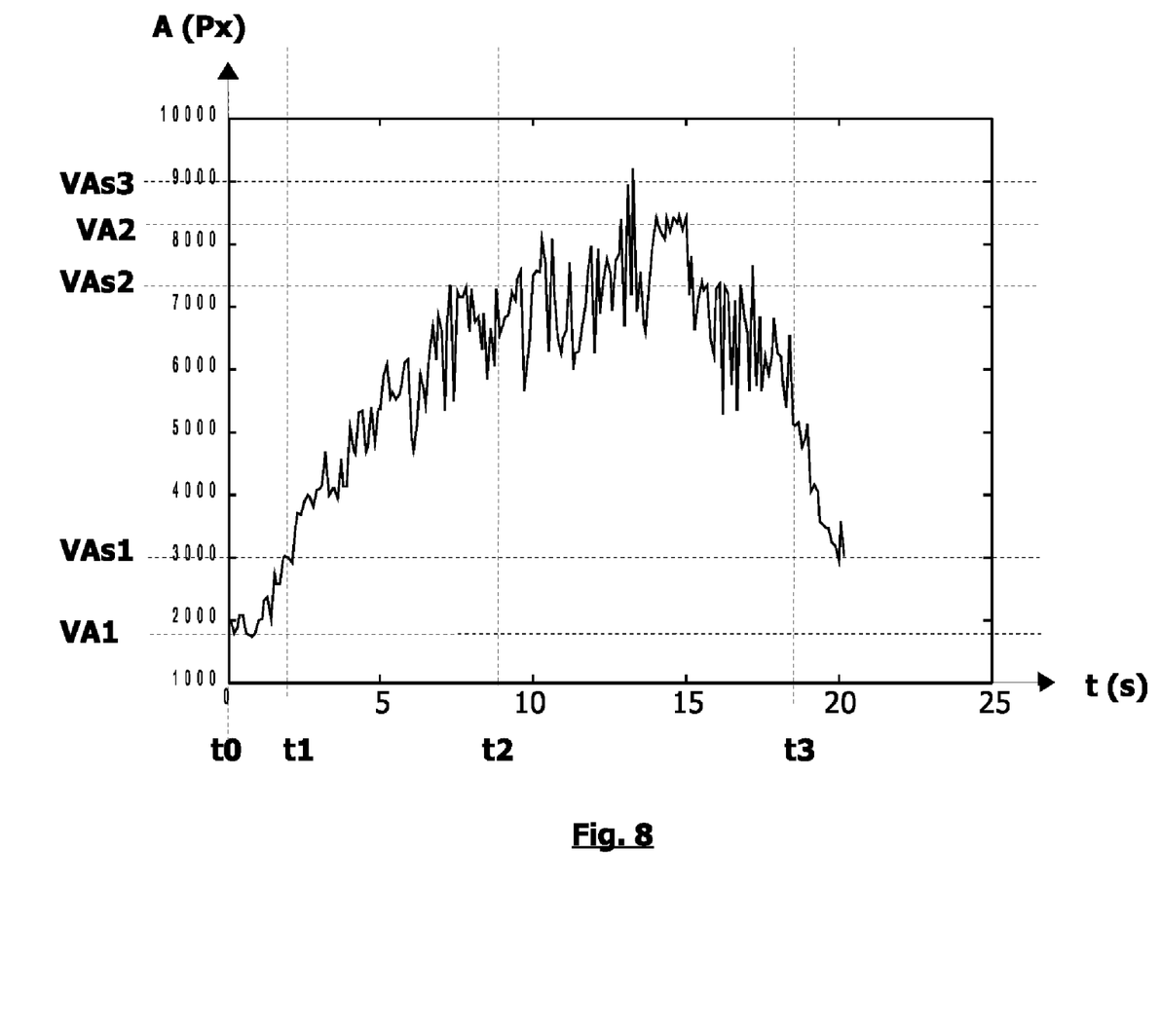
FIG. 8 illustrates a variation as a function of the time of the area within a graph of levels of grey calculated by the process shown in FIG. 1.

FIG. 8 illustrates a non-limiting example of a variation of the area A determined in a graph of the different levels of grey over a period of time, that is to say in a sequence SQ of captured images I.

The time is shown in seconds in the abscissa and the area is shown in pixels in the ordinate.

At the time t0=0, the value of the area A represents the absence of fog. In a non-limiting example, the value VA1 is shown to be equivalent to 1777 pixels, which corresponds to the area A1 in the reference graph of different levels of grey CL1 without the presence of fog F indicated above in FIG. 6.

As the images are captured, the value of the area A changes in relation to the variations within the atmosphere around the vehicle and also the atmosphere in front of the vehicle, and thereby in relation to the presence or the absence of fog F in the area in which the vehicle is presently located or is about to enter.

In this way, it can be seen that between the times t0 and t1, the value of the area A increases and becomes greater than a first threshold value VAs1. From this is can be deduced that t1 represents an entry into an area having fog F.

The vehicle V has not yet reached the fog F but has detected that it is approaching this area.

In this way, the progressive variations of the area A indicate that an area containing fog is approaching and is about to be entered. The detection of fog F can therefore be anticipated as a result of the use of the front camera.

In a non-limiting example, the first threshold value VAs1 is equal to 3000. Above this value, it can be estimated that noise is present in the signal.

Between the times t2 and t3, the value of the area A is greater than a second threshold value VAs2 which is characteristic of fog F.

The vehicle is thus in an area containing fog F.

In a non-limiting example, this value Vas2 is situated at a level of about 7000 pixels and corresponds to a fog or moderate density.

The value VA2 equivalent to 8057 pixels for example corresponds to the area A2 in the graph of the different levels of grey CL2 with fog F represented as above in FIG. 7 and is thus situated above this second threshold VAs2.

Above the time t3, the value of the area A once again falls to below the threshold value VAs2 and then reduces progressively. From this, it can be deduced that the vehicle is leaving the area containing fog F.

A third threshold value VAs3 is used to establish that the fog F in which the vehicle V is located is of a high density. In a non-limiting embodiment, this third threshold value VAs3 is higher than 9000 pixels.

It will be noted that in the example contained in FIG. 8, this value is never reached.

In a second embodiment, both the presence of fog F and its density can be detected in relation to a visibility distance DVM, with this latter being determined in relation to the specific area A referred to above.

In a non-limiting embodiment, when the area that is used represents the top of the captured image I to the horizon line H, the relationship between the visibility distance DVM and the area A in question is equal to:

$$DVM = 275 - A*15/600. \quad [1]$$

It will be noted that, in this case, this equation [1] does not depend on the type of bitumen used, the quality of the road surface or any other characteristic of the road as described above.

Clearly, other coefficients could be used.

Both the presence and the density of fog F can be deduced from the visibility distance calculated in this manner.

In this way, in a non-limiting embodiment, when the visibility distance is less than 150 meters, the presence of fog F can be deduced.

Moreover, with regard to the density, if the visibility distance is less than 60 meters, it can be deduced that the density of the fog F is high, whereas if it is greater than 60 meters and above, it can be deduced that the density of the fog F is either moderate (60-100 meters) or low (100-150 meters).

The calculation of the visibility distance DVM thus can provide the driver of the vehicle V with information on the maximum speed Vmax that he should not exceed if he is to drive safely and it can therefore also guarantee an optimum safety distance. In a non-limiting example, at a speed of 90 km/h, it is known that the stopping distance is about 80 meters.

Clearly, these two modes (the use of the thresholds VAs and the calculation of the distance visibility DVM) can be combined either in parallel or in sequence.

In a seventh step 7), after the fog F has been detected, its density determined and—where necessary—after the visibility distance DVM has been calculated, an appropriate treatment CD in real time can be carried out on the vehicle V.

In a number of non-limiting examples, this can be a question of:
  automatically adapting the beam of the headlamps PJ of the vehicle V by increasing the intensity of the low beam or the high beam of the headlamps PJ (for example, to increase the visualization of the white lines on the road) and/or by activating the fog lamps (front and rear); or
  sending an alert signal to the driver of the vehicle V so that he himself increases the intensity of the headlamps PJ, for example either by increasing the brightness or by switching on his fog lamps; or
  automatically switching the headlamp beam from high beam to low beam or vice versa; or
  automatically reducing the speed of the vehicle to a maximum authorized speed Vmax in this case; or
  sending an alert signal to the driver of the vehicle V to advise him to reduce his speed relative to a maximum authorized speed or relative to a distance for stopping the vehicle V, etc.

Depending on the density of the fog F, the following can be determined in non-limiting examples:
  a threshold for the activation of the fog lamps for a given visibility distance DVM; and
  an automatic switching threshold of the low beam and high beam headlamps PJ for a visibility distance DVM greater than or equal to a given threshold; or
  an automatic switching threshold of the low beam and high beam headlamps PJ for a visibility distance DVM less than a given threshold etc.

It will be noted that these different thresholds can be defined in non-limiting examples on the basis of existing regulations or in accordance with a manufacturer's standard.

It will be noted that this seventh step is effected at the same time that the processing of the video images I is carried out by the process described above.

In this way, the appropriate treatment CD, such as, for example, the automatic adjustment of the headlamp beam PJ to either a low beam or a high beam setting, is carried out in real time, as it is carried out whenever an phenomenon F limiting the visibility is detected, with each such detection occurring with each capture of an image I.

It will also be noted that the treatment CD can obviously be carried out using:
  the visibility distance DVM without using the thresholds VAs of a graph of the different levels of grey; or
  the thresholds VAs of a graph of the different levels of grey CL without using the visibility distance DVM; or
  both the visibility distance DVM and the thresholds VAs of a graph of the different levels of grey CL.

Figure 9:
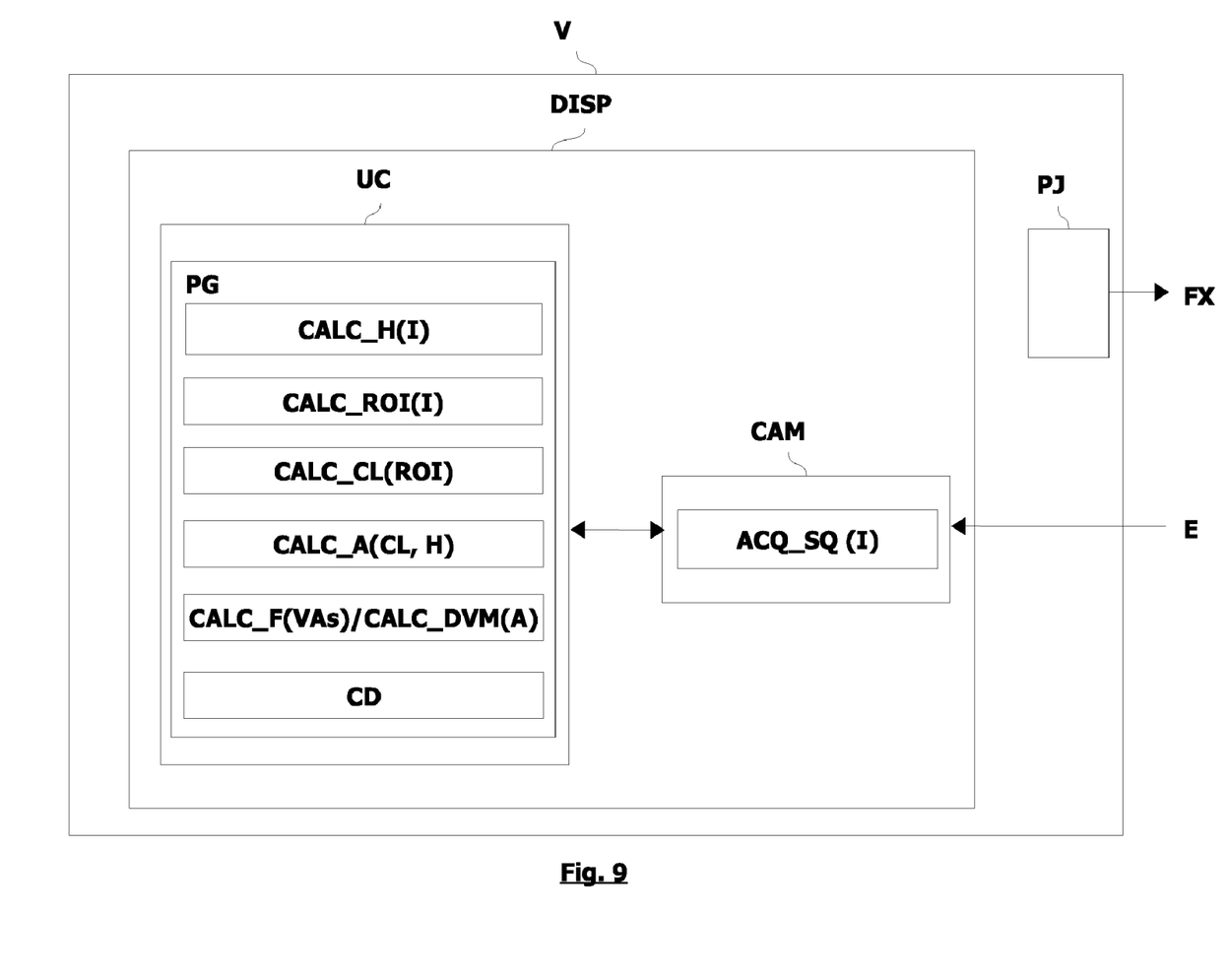
FIG. 9 illustrates a non-limiting embodiment of a device for the implementation of the process shown in FIG. 1.

The process according to the present invention is put into practice by a detection device DISP illustrated in FIG. 9.

This device DISP is installed in the vehicle V and comprises in particular:
  A control unit UC to:
    determine at least one point of interest H in an image I captured of the surroundings E of the vehicle V;
    determine a region of interest ROI in the image I;
    determine a graph of the different levels of grey CL from the region of interest ROI; and
    determine an area (A) in the graph of the different levels of grey (CL) in relation to the given point of interest (H).

The control unit UC also allows the control of the headlamp PJ and the camera CAM and also the control (automatic adjustment of the headlamp beam PJ into either a low beam or a high beam mode, automatic switching of the fog lamps) or it can carry out (by sending an alert signal) the appropriate treatment CD.

In one non-limiting embodiment, the detection device DISP can also include the video camera CAM, enabling an image I as illustrated in FIG. 9 to be captured. It will be noticed that in this case the control unit UC can also be installed in the video camera CAM.

The camera CAM is located in a non-limiting example behind the windscreen of the vehicle V. In a further non-limiting example, the camera CAM is placed near one of the headlamps PJ of the vehicle V.

It is, for example, of the VGA type with a definition of 640*480 (in other words, a captured image I of 8 bits (per pixel) comprising 640 columns and 480 lines) and comprises a lens (not shown) for this purpose. The image I thus captured is in full resolution.

A specific value GR is attributed to each pixel Px. This value is known as the value of the level of grey on the basis of the processing operations used in the camera (management of the integration time, of the response curve of the camera, the gain etc.). This value of the level of grey can be expressed in different formats, for example, in 8 bits, 12 bits or in any other form.

For example, the level of grey of the pixel in 8 bits can be between 0 and 255, while the level of grey of the pixel in 12 bits can be between 0 and 4095.

In one non-limiting embodiment, the video camera CAM captures 10 images per second.

Clearly, a different type of camera with a different resolution can be used.

Clearly, the camera CAM used for the purpose of detecting fog F can also be used for other known functions, such as:
  the detection of lines marking the road (thereby enabling an involuntary crossing of the lines to be avoided); or
  the automatic switching of low beam and high beam headlamps or switching back again in the event of oncoming vehicles (preventing dazzling oncoming traffic) etc.

It will also be noted that all of the steps of the process described above are effected for one or more (sequences SQ) images I captured by the video camera CAM and this in real time. That is to say, that the totality of the steps does not take more than ¹⁄₁₀th second in the example of a sequence of 10 images per second captured by the camera CAM. This process is thus very fast.

It will be noted that the implementation of the detection process described above can be effected by means of a microdevice programmed with software, a cabled logical system and/or electronic hardware components.

In this way, the detection device DISP can comprise a computer program product PG comprising one or more sequences of instructions that can be carried out by a data processing unit, such as a microprocessor, or the processing unit of a micro-controller, an ASIC or a computer etc., with the execution of said sequences of instructions enabling the process to be operated.

Such a computer program PG can be stored in a non-volatile inscribable memory of the ROM type, or in a non-volatile re-inscribable memory of the type EEPROM or FLASH. The computer program PG can be inscribed into the memory during manufacturing or loaded into the memory or remotely loaded into the memory. The sequences of instructions can be sequences of machine instructions, or alternatively the sequences of a control language interpreted by the processing unit at the time of their implementation.

In the non-limiting example shown in FIG. 9, the computer program PG is inscribed in a memory of the control unit UC of the device DISP.

Clearly, the description of the process is not limited to the different embodiments and examples described above.

In this way, the process described above can also be used with the camera mounted at the rear and with the rear lamps to effect the appropriate treatment CD, such as for example, activating the fog lamps.

Furthermore, if the region of interest ROI that was determined is not sufficiently homogenous, it is possible not to use it and to await for the determination of the region of interest ROI on the subsequent captured image I.

Finally, it can clearly be applied to different applications than that of the motor vehicle described above.

The present invention thus has the following advantages:
it enables the presence of a phenomenon F limiting the visibility to be detected, such as fog and to initiate an appropriate treatment CD;
it enables the density of the fog F to be calculated;
it enables the visibility distance DVM to be determined for the user of the vehicle V;
it is simple to put into practice (the determination of a region of interest, of the horizon line H, of a graph of the different levels of grey and the associated area are easy to process);
it can be easily integrated into a lighting and signaling system such as a signal lamp or a headlamp (camera, software/hardware) without the installation of any cumbersome equipment on the chassis of the vehicle;
it enables the presence of fog to be anticipated by the advance detection of an oncoming patch of fog before the vehicle enters it; and
it therefore prevents the need for two cameras to be used, one for the detection of a phenomenon limiting the visibility and one for the detection of the road markings, for example. In this way, both functions are carried out by a single camera, which is multifunctional.

While the processes and products herein described constitute preferred embodiments of this invention, it is to be understood that the invention is not limited to these precise processes and products, and that changes may be made therein without departing from the scope of the invention which is defined in the appended claims.

What is claimed is:

1. A process for detecting a phenomenon (F) limiting the visibility in the environment (E) of a motor vehicle (V) comprising the following steps:
    emitting a beam (FX) from at least one of the headlamps (PJ) of the vehicle (V) into the environment (E) of the vehicle (V);
    determining at least one point of interest (H) in an image (I) captured on the environment (E) of the vehicle (V);
    determining a region of interest (ROI) in said image (I);
    determining a graph of different levels of grey (CL) from said region of interest (ROI); and
    determining an area (A) in said graph of different levels of grey (CL) in relation to the determined point of interest (H).

2. The process in accordance with claim 1, wherein the process contains a supplementary step for:
    determining the presence of a phenomenon (F) limiting the visibility in relation to at least one threshold value (VAs) of said area (A).

3. The process in accordance with claim 1, wherein the process contains a supplementary step for:
    determining a visibility distance (DVM) in relation to said area (A).

4. The process in accordance with claim 1, wherein the point of interest (H) is situated on the horizon line in the image (I).

5. The process in accordance with claim 1, wherein the vehicle (V) has a steering angle ($\alpha$), and said region of interest (ROI) is determined in said image (I) in relation to said steering angle.

6. A device (DISP) for the detection of a phenomenon (F) limiting the visibility in the environment (E) of a motor vehicle comprising:
    at least one headlamp (PJ) for:
        emitting a light beam (FX) into the environment (E) of the vehicle (V);
    a control unit (UC) for:
        determining at least one point of interest (H) in an image (I) captured of the environment (E) of the vehicle (V);
        determining a region of interest (ROI) in said image (I);
        determining a graph of different levels of grey (CL) on the basis of said region of interest (ROI); and
        determining an area (A) in said graph of different levels of grey (CL) in relation to said point of interest (H).

7. A non-transitory computer program product (PG) adapted to perform the process according to claim 1.

8. The process in accordance with claim 2, wherein the process contains a supplementary step for:
    determining a visibility distance (DVM) in relation to said area (A).

9. The process in accordance with claim 2, wherein the vehicle (V) has a steering angle ($\alpha$), and said region of interest (ROI) is determined in said image (I) in relation to said steering angle.

10. The process in accordance with claim 3, wherein the vehicle (V) has a steering angle ($\alpha$), and said region of interest (ROI) is determined in said image (I) in relation to said steering angle.

11. The process in accordance with claim 4, wherein the vehicle (V) has a steering angle ($\alpha$), and said region of interest (ROI) is determined in said image (I) in relation to said steering angle.

12. The process in accordance with claim 1, wherein said process comprises the step of:
    adjusting said headlamps in response to said determining steps.

13. The process in accordance with claim 12, wherein said process comprises the step of:
   automatically adjusting said headlamps in response to said determining steps.

14. The device in accordance with claim 6, wherein said control unit adjusts at least one headlamp in response to said determining steps.

15. The device in accordance with claim 14, wherein said control unit automatically adjusts at least one headlamp in response to said determining steps.

* * * * *